(12) United States Patent
Yan et al.

(10) Patent No.: US 11,525,829 B2
(45) Date of Patent: Dec. 13, 2022

(54) METHOD FOR CAPTURING TARGET CELLS OR MOLECULES IN SOLUTION

(71) Applicant: Hemosmart Medical Technology Ltd., Jiangsu (CN)

(72) Inventors: Jing Yan, Jiangsu (CN); Jerome Charmet, Coventry (GB); Bauer Wolfgang-Andreas Christian, Jiangsu (CN); Ziyi Yu, Jiangsu (CN); Yang Yang, Jiangsu (CN)

(73) Assignee: Hemosmart Medical Technology Ltd., Jiangsu (CN)

( * ) Notice: Subject to any disclaimer, the term of this patent is extended or adjusted under 35 U.S.C. 154(b) by 499 days.

(21) Appl. No.: 16/625,658

(22) PCT Filed: Aug. 2, 2017

(86) PCT No.: PCT/CN2017/095558
§ 371 (c)(1),
(2) Date: Dec. 20, 2019

(87) PCT Pub. No.: WO2019/023961
PCT Pub. Date: Feb. 7, 2019

(65) Prior Publication Data
US 2020/0150114 A1    May 14, 2020

(51) Int. Cl.
*B01L 3/00* (2006.01)
*G01N 33/543* (2006.01)
(Continued)

(52) U.S. Cl.
CPC ....... *G01N 33/54393* (2013.01); *C12M 47/04* (2013.01); *G01N 15/0631* (2013.01)

(58) Field of Classification Search
CPC ....... G01N 33/54393; G01N 33/54366; G01N 33/5438; C12M 47/04; C12M 41/36; C12M 23/12
(Continued)

(56) References Cited

U.S. PATENT DOCUMENTS 7,855,068 B2    12/2010    Cao
2004/0219547 A1*    11/2004    Frey .................. C12Q 1/00
                                                                435/6.1
(Continued)

FOREIGN PATENT DOCUMENTS

CN    102978105    3/2013
CN    105504301    4/2016
(Continued)

OTHER PUBLICATIONS

International Search Report and Written Opinion issued in PCT Application No. PCT/CN2017/095558, dated Apr. 26, 2018, in 8 pages.

*Primary Examiner* — Hoa Q Pham
(74) *Attorney, Agent, or Firm* — Knobbe, Martens, Olson & Bear, LLP

(57) ABSTRACT

Disclosed is a method for capturing target cells or molecules in solution, comprising steps of: (I) getting medium containing said target cells or molecules into an apparatus comprising a capturing device for capturing said target cells or molecules; (II) getting said medium flow through said capturing device; (III) removing unbound debris, cells and molecules; (IV) getting said target cells or molecules detached from the capturing device; and (V) collecting said target cells or molecules; wherein said capturing device comprises at least one functionalized mesh comprising a mesh substrate and a functional layer formed on said mesh substrate, wherein said functional layer comprises capturing substances that can specifically bind with said target cells or
(Continued)

molecules. The method has high specificity, as well as high throughput, and is suitable for capturing cells or molecules in a solution or expressed at the surface of cell membranes. It is particularly suited to capture and sort circulating tumor cells.

20 Claims, 6 Drawing Sheets

(51) Int. Cl.
*C12M 1/00* (2006.01)
*G01N 15/06* (2006.01)

(58) Field of Classification Search
USPC ............. 422/61, 68.1, 50, 57–58; 435/287.1, 435/287.2, 287.9, 288.5; 436/501
See application file for complete search history.

(56) References Cited

U.S. PATENT DOCUMENTS

| 2020/0156073 A1* | 5/2020 | Yan | .......................... C12M 47/04 |
| 2021/0198612 A1* | 7/2021 | Yan | .......................... C12M 47/04 |

FOREIGN PATENT DOCUMENTS

| CN | 205501298 | 8/2016 |
| CN | 205501299 | 8/2016 |
| CN | 106635769 | 5/2017 |
| CN | 107338184 | 11/2017 |
| CN | 107338185 | 11/2017 |
| WO | WO 2010/108003 | 9/2010 |
| WO | WO 2012/051390 | 4/2012 |
| WO | WO 2014/153262 | 9/2014 |

* cited by examiner

METHOD FOR CAPTURING TARGET CELLS OR MOLECULES IN SOLUTION

CROSS-REFERENCE TO RELATED APPLICATIONS

This application is the U.S. National Phase under 35. U.S.C. § 371 of International Application PCT/CN2017/095558, filed Aug. 2, 2017, the disclosure of which including the specification, the drawings, and the claims is hereby incorporated by reference in its entirety.

TECHNICAL FIELD OF THE INVENTION

The present disclosure relates to method for capturing target cells or molecules, in particular to a method for capturing target cells (e.g. circulating tumor cell) via molecules expressed by said cells or molecules in solution.

BACKGROUND OF THE INVENTION

Circulating tumor cells (CTCs), which are tumor cells in blood circulation, are considered as having a major relationship with issues such as distant metastasis of tumor. Generally, there is only 1 to 10 CTC(s) in 10 ml blood of cancer patients. Current bottlenecks hindering a rapid detection of cells from blood samples of patients are the low throughput and poor efficiency of capturing devices and methods.

Presently there are several methods for sorting cells, such as the traditional magnetic activated cell sorting method (MACS), membrane microfiltration technology, density gradient centrifugation technology and microfluidic technology etc. The traditional magnetic activated cell sorting method has good reproducibility, high sensitivity and specificity, and is capable of analyzing CTCs quantitatively, however it is unfavorable because of its low operation speed and throughput. The membrane microfiltration and the density gradient centrifugation technologies are simple to operate and enable the capture of cells, however it has low specificity and high false positive rate. There exist different microfluidic enabled CTC sorting/capturing devices. Devices with functionalized posts or devices relying on separation techniques using acoustic, electrophoretic or centrifuge separation and filtration membranes have been used in microfluidic devices. Those devices are simple in operation and require fewer antibodies, but their cost and false negative rate are high and throughput low. Also, presently microfluidic technology companies are mainly focusing on research customers. The method requires mixing a variety of reagents in advance and is over-reliant on fabrication techniques that are not easily transferable to medium to large-scale manufacturing, thus the devices are difficult to industrialize and not easily applicable to in vitro diagnosis.

Also, there is a Cell Search device provided by a US company. This device has advantages of high sensitivity and specificity, but its blood consumption is large, the required amount of antibodies and cost are high, it fails to capture living cells and cannot be used to collect and re-culture CTCs. Consequently, it can be used for DNA sequencing but not for RNA sequencing and medication guidance.

SUMMARY OF THE INVENTION

One purpose of the present disclosure is to provide a method for capturing target cells or molecules in solution. The method of the invention has high specificity, as well as high throughput and is suitable for capturing cells via molecules expressed by said cells or molecules in solution. It is particularly suited to capture and sort circulating tumor cells.

The technical solutions employed by the present invention present disclosure are: a method for capturing target cells or molecules in solution, comprising steps of:

(I) getting medium containing said target cells or molecules into an apparatus comprising a capturing device for capturing said target cells or molecules;

(II) getting said medium flow through said capturing device so that said target cells or molecules bind to the capturing device;

(III) removing unwanted unbound debris, cells or molecules that may have interacted non-specifically on said capturing device;

(IV) getting said target cells or molecules detached from said capturing device; and (V) collecting said target cells or molecules;

wherein said capturing device comprises at least one functionalized mesh, said functionalized mesh comprises a mesh substrate and a functional layer formed on said mesh substrate, wherein said functional layer comprises capturing substances that can specifically bind with said target cells or molecules.

Preferably, in the step of (I), said medium is flown into said apparatus by injection or pumping.

Preferably, in the step of (II), said medium is made to flow through said capturing device a couple of times before flowing out of the apparatus.

Further preferably, said injection or pumping is reversible, said medium is firstly made to flow positively through said capturing device and then made to flow reversely through said capturing device.

Preferably, in the step of (III), rinsing said capturing device in ultra-pure water or other mild solvent to remove said unbound debris, cells or molecules.

Preferably, in the step of (IV), injecting cell detachment buffer to get the cells or molecules detached from said capturing device.

Further preferably, in the step of (IV), said cell detachment buffer contains trypsin.

Preferably, in the step of (V), said target cells or molecules are counted.

Further, preferably, in the step of (V), counting of said molecules is achieved by electrodes using impedance measurement or other counting methods such as optical methods (with or without fluorescent tags). Said electrodes for impedance measurement are arranged in a microfluidic channel provided inside of said apparatus, and said target cells or molecules are collected through the microfluidic channel.

Preferably, said target molecules are proteins, oligonucleotides (DNA and/or RNA), enzymes or any combination thereof in a solution or expressed at the surface of cell membranes.

Further preferably, said target molecules are epithelial cell adhesion molecules expressed at the surface of circulating cancer cells.

Further, preferably, said capturing substances are anti-epithelial cell adhesion molecule antibodies, which can specifically bind with said epithelial cell adhesion molecule.

Specially, said anti-epithelial cell adhesion molecule antibodies are attached to said mesh substrate by traut's reagent or thiolated molecules with biotin-avidin.

Preferably, said capturing substances are selected from the group consisting of antibodies (including nanobodies), oligonuecleotides (including aptamer) and molecularly imprinted polymers.

Further preferably, said capturing substances are attached to said mesh substrate by physical adsorption and/or chemical bonding, said chemical bonding is achieved by using thiolated molecules with or without a linker, using traut's reagent, silanisation or click chemistry.

Preferably, said mesh substrate is 2-10 mm×2-10 mm in size and said opening of said mesh is 20 μm-100 μm.

Preferably, said mesh substrate comprises:
a stainless steel body; and
a surface coating provided on the surface of said stainless steel body; wherein said surface coating is made of gold or other noble metal or alloy thereof (such as AuPd), and said capturing substances are attached to said surface coating.

Further preferably, said surface coating is deposited using magnetron sputtering or electrochemistry.

Preferably, said capturing device containing multiple functionalized meshes stacked together.

Preferably, said apparatus further comprises a body which has an inlet, a first outlet and a cavity located between said inlet and said first outlet, said capturing device is fixed inside said cavity, said inlet and said first outlet communicate with the cavity, and
in the step of (I), getting said medium into said cavity of apparatus through said inlet; and
in the step of (III), removing unbound molecules, cells or debris and molecules through said first outlet.

Preferably, the body is fabricated using established manufacturing technique such as injection moulding. The material of the body should also be compatible with solvents. For example, PEEK (polyetheretherketone) would fulfill both conditions.

Preferably, in the step of (V), collecting said target cells or molecules through a microfluidic channel provided inside of said body communicated with said cavity.

Due to the use of the above technical solutions, the present invention present disclosure has the following advantages and effects over the prior art:
Easier functionalization and higher throughput compared to microfluidic device using functionalized surfaces;
No risk of clogging compared to microfluidic device using microfilters;
higher specificity;
Potentially higher efficiency compared to all other techniques;
Possibility to collect the cells after the assay.

Wherein: 1-body; 10-cavity; 101-upper cavity; 102-lower cavity; 11-inlet; 12-first outlet; 13-microfluidic channel; 14-second outlet;
2-capturing device; 20-mesh; 201-stainless steel body; 202-surface coating; 21-antibodies; 22-functional layer;
3-counting device; 30-electrode;
4-circulating cancer cell; 5-blood cell.

DETAILED DESCRIPTION OF EXEMPLARY EMBODIMENTS

In the following, the present invention is described in detail combining with the accompanying drawings and embodiments.

In the following, the present disclosure is described in detail combining with the accompanying drawings and embodiments.

A method for capturing target cells or molecules in solution is provided by the present disclosure, wherein the target molecules are in solution or expressed at the surface of cell membranes. The method comprises steps of:
(I) getting medium containing target cells or molecules into an apparatus comprising a capturing device for capturing target cells or molecules;
(II) getting said medium flow through said capturing device so that target cells or molecules bind to the capturing device;
(III) removing unwanted unbound debris, cells or molecules that may have bound non-specifically on said capturing device;
(IV) getting target cells or molecules detached from said capturing device; and
(V) collecting target cells or molecules.

Specifically, in the step of (I), the medium is flown into the apparatus by injection or pumping. In the step of (II), the medium is made to flow through the capturing device a couple of times before flowing out of the apparatus, and more specifically, said injection or pumping is reversible, so that the medium is firstly made to flow positively through the capturing device and then made to flow reversely through the capturing device. In the step of (III), rinsing the capturing device in ultra-pure water to remove the unbound debris, cells or molecules. In the step of (IV), injecting cell detachment buffer containing trypsin to get the cells or molecules detached from the capturing device. In the step of (V), the target cells and molecules are further analyzed. Typically, the cells are counted and then collected for further analysis. The method can capture any target cells or molecules and these molecules can either be "floating" in a solution (biofluid or else) or attached to a cell (in this case, it will be capturing the cells).

Figure 1:
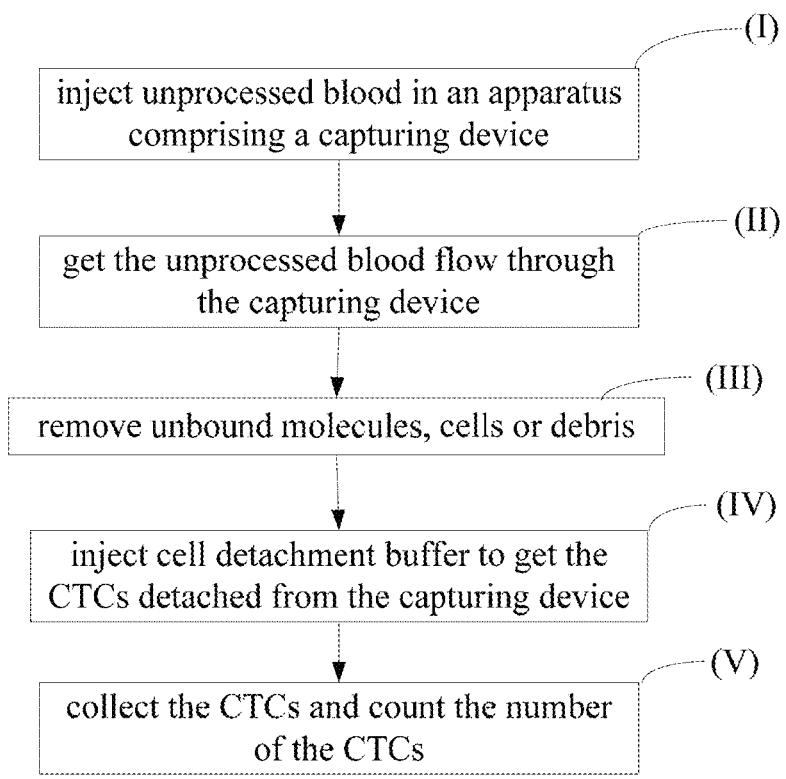
FIG. 1 is a flow diagram of the method for capturing molecules at the surface of circulating tumor cells.

For instance, the target molecules are epithelial cell adhesion molecules at the surface of the circulating cancer cells, so the method is used for rapidly capturing circulating cancer cells. As shown in FIG. 1, in the step of (I), inject unprocessed blood (i.e. said medium containing target cells or molecules) in an apparatus comprising a capturing device for capturing CTCs; in the step of (II), get the unprocessed blood flow through the capturing device so that epithelial cell adhesion molecules of the CTCs bind to the capturing device; in the step of (III), remove unwanted debris, blood cells, molecules or the combination thereof, possibly remaining on the capturing device through non-specific interaction; in the step of (IV), inject cell detachment buffer to get the CTCs detached from the capturing device; and in the step of (V), collect the CTCs and count the number of the CTCs.

Figure 2:
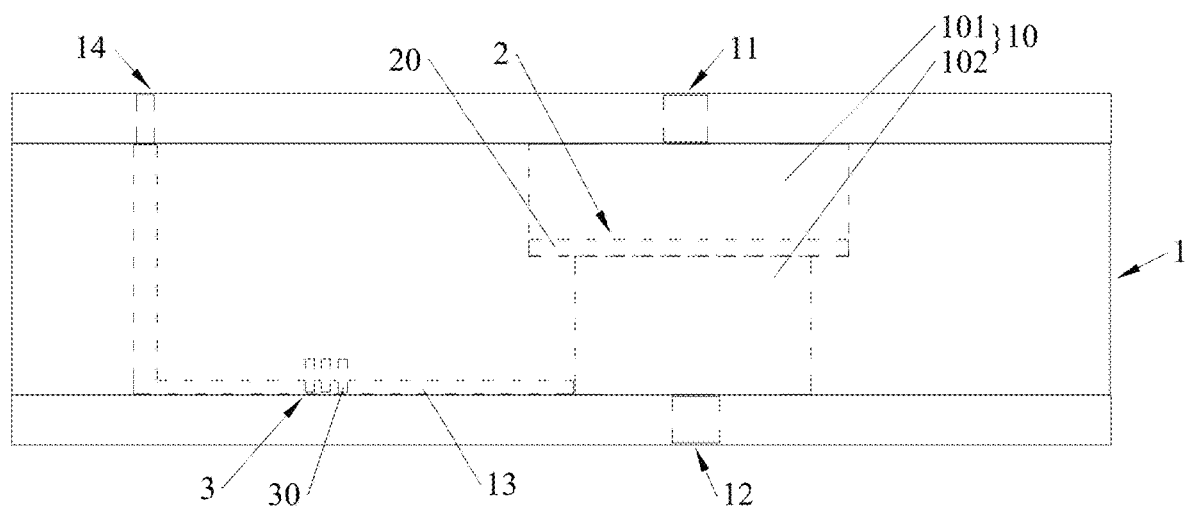
FIG. 2 is a schematic view of the apparatus for capturing molecules according to the present disclosure.
Figure 3:
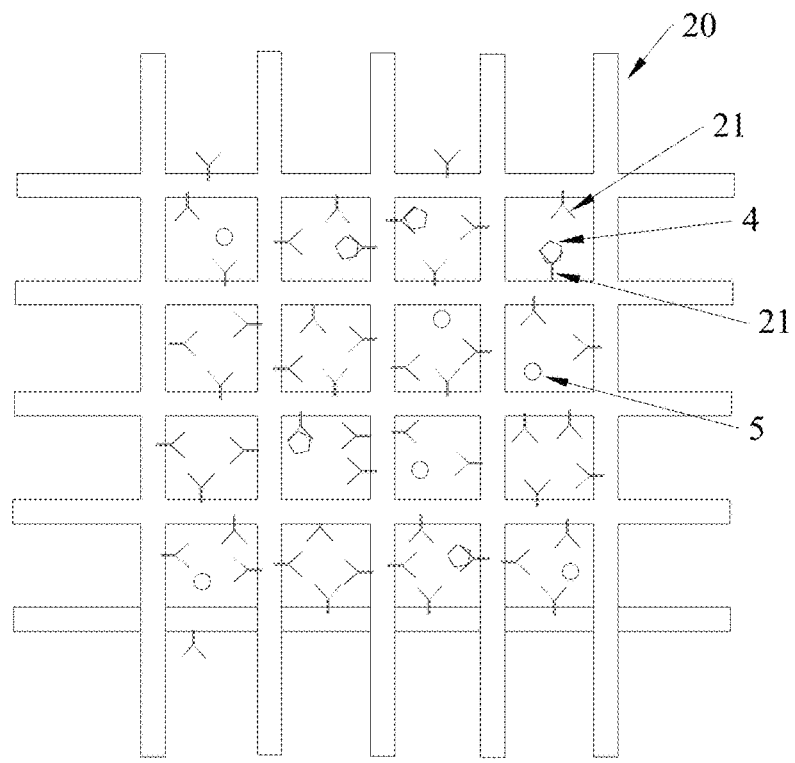
FIG. 3 is a schematic view of the functionalized mesh according to the present disclosure with captured CTCs.
Figure 4:
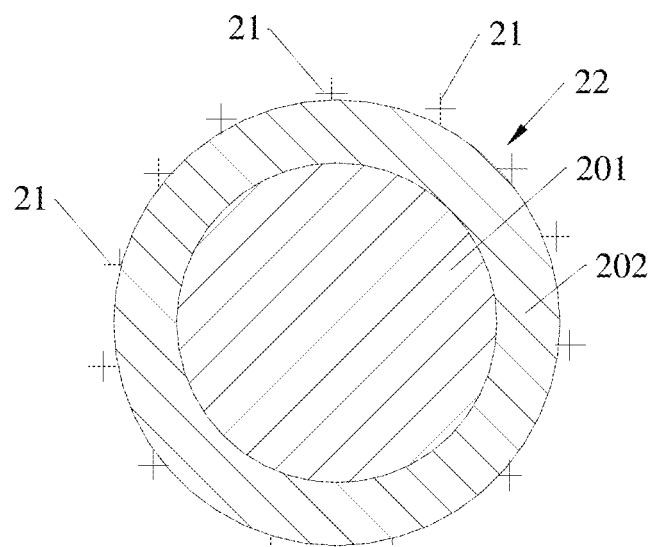
FIG. 4 is a section view of part of the functionalized mesh according to the present disclosure.

Said apparatus is shown in FIGS. 2-4 and will be described below in detail. The apparatus disclosed in the present invention relies on using one or more functionalized mesh(s) to capture circulating tumor cells (CTCs) in a hybrid macro/micro-fluidic device (FIG. 2). The "macro" part is used to optimize the capture by increasing the capture area while minimizing the time of the assay. The "micro" part will be used to detect and collect the CTCs.

FIG. 2 shows an exemplary embodiment of the apparatus for capturing CTCs, more specifically, the epithelial cell adhesion molecules at the surface of the circulating cancer cells. The apparatus comprises:

a body 1 with a cavity 10 inside and having an inlet 11 and a first and second outlet 12 and 14;

a capturing device 2 comprising at least one functionalized mesh 20; and a counting device 3;

Wherein, the body 1 is fabricated using established manufacturing technique such as injection moulding. The material of the body should also be compatible with solvents. For example, PEEK (polyetheretherketone) would fulfill both conditions. Preferably the body 1 is manufactured by injection moulding to form the cavity 10. The capturing device 2 is arranged in the cavity 10. The inlet 11 and the first outlet 12 are set at two ends of the cavity respectively and communicated with the cavity 10, and the capturing device 2 is located inside the cavity 10 and between the inlet 11 and the first outlet 12.

More specifically, the inlet 11 is opened on the top surface of the body 1 and the first outlet 12 is opened on the bottom surface of the body 1, i.e. the inlet 11 is above the capturing device 2 and the first outlet 12 is below the capturing device 2. The cavity 10 is divided into two parts namely the upper cavity 101 (or the first cavity) and the lower cavity 102 (or the second cavity) by the capturing device 2. Both the upper cavity 101 and the lower cavity 102 are cuboid and the cross section area along horizontal direction of the upper cavity 101 is larger than that of the lower cavity 102. The functionalized mesh 20 of the capturing device 2 is prepared to have capturing substances that can specifically bind with target cells or molecules expressed by the cells at their membrane using any affinity base technique. Target cells or molecules in medium especially solution (e.g. unprocessed blood) can be led into the upper cavity 101 through the inlet 11 and then flow through the capturing device 2 to the lower cavity 102 and finally flow out of the body 1 through the first outlet 12. During this process, target cells or molecules are captured by the capturing device 2 while other part of the blood go through the capturing device 2 untrapped. The advantage of the functionalized mesh is the high surface to volume ratio allowing the processing of large volume of samples while minimizing the risk of clogging. Once the target cells or molecules have been captured, they can be released (e.g. chemically, thermally, electrically) for further analysis or diagnosis. The capturing device 2 may consist of multiple functionalized meshes stacked together.

As shown in FIG. 3, a functional layer 22 comprises antibodies 21, which can capture molecule of circulating cancer cell and expressed by circulating cancer cell are attached to each mesh substrate. Preferably, the antibodies 21 are anti-epithelial cell adhesion molecule (anti-EpCAM) antibodies. The anti-epithelial cell adhesion molecule antibodies can bind with molecule, specifically, epithelial cell adhesion molecule (EpCAM), at the surface of circulating cancer cells. It can be seen from FIG. 3 that circulating cancer cells 4 are bound to the antibodies 21 on the mesh 20 while other blood cells 5 are free from the mesh 20.

Material of the mesh substrate can be selected from gold or other noble metals and stainless steel coated with gold or other noble metals. Preferably, as shown in FIG. 4, the functionalized mesh substrate comprises:

a stainless steel body 201 and a surface coating 202 provided on the body 201.

Material of the mesh 20 can be selected from gold or other noble metals and stainless steel coated with gold or other noble metals. Preferably, as shown in FIG. 4, the functionalized mesh 20 comprises:

a stainless steel body 201 and a surface coating 202 provided on the body 201. The material of the surface coating 202 is gold or noble metal of alloy thereof (e.g. AuPd), and the antibodies 21 are attached to the surface coating 202. The surface coating 202 is AuPd coating deposited on the body 201 by using magnetron sputtering or electrochemistry. The anti-epithelial cell adhesion molecule antibodies are attached to the mesh 20 by Traut's reagent, or thiolated biotin-avidin linker instead of Traut's reagent.

A microfluidic channel 13 is also provided inside of the body 1, which is communicated with the lower cavity of the cavity 10 through which circulating cancer cells captured by the mesh 20 can be collected, after they are detached from the mesh 20 by cell detachment buffer. The counting device 3 is arranged in the microfluidic channel 13 for counting the numbers of captured circulating cancer cells. The counting device 3 comprises electrodes 30 for impedance measurement. The second outlet 14 opened on the top surface of the body 1 is communicated with the microfluidic channel 13 for captured circulating cancer cells flowing out of the body 1.

Figure 5:
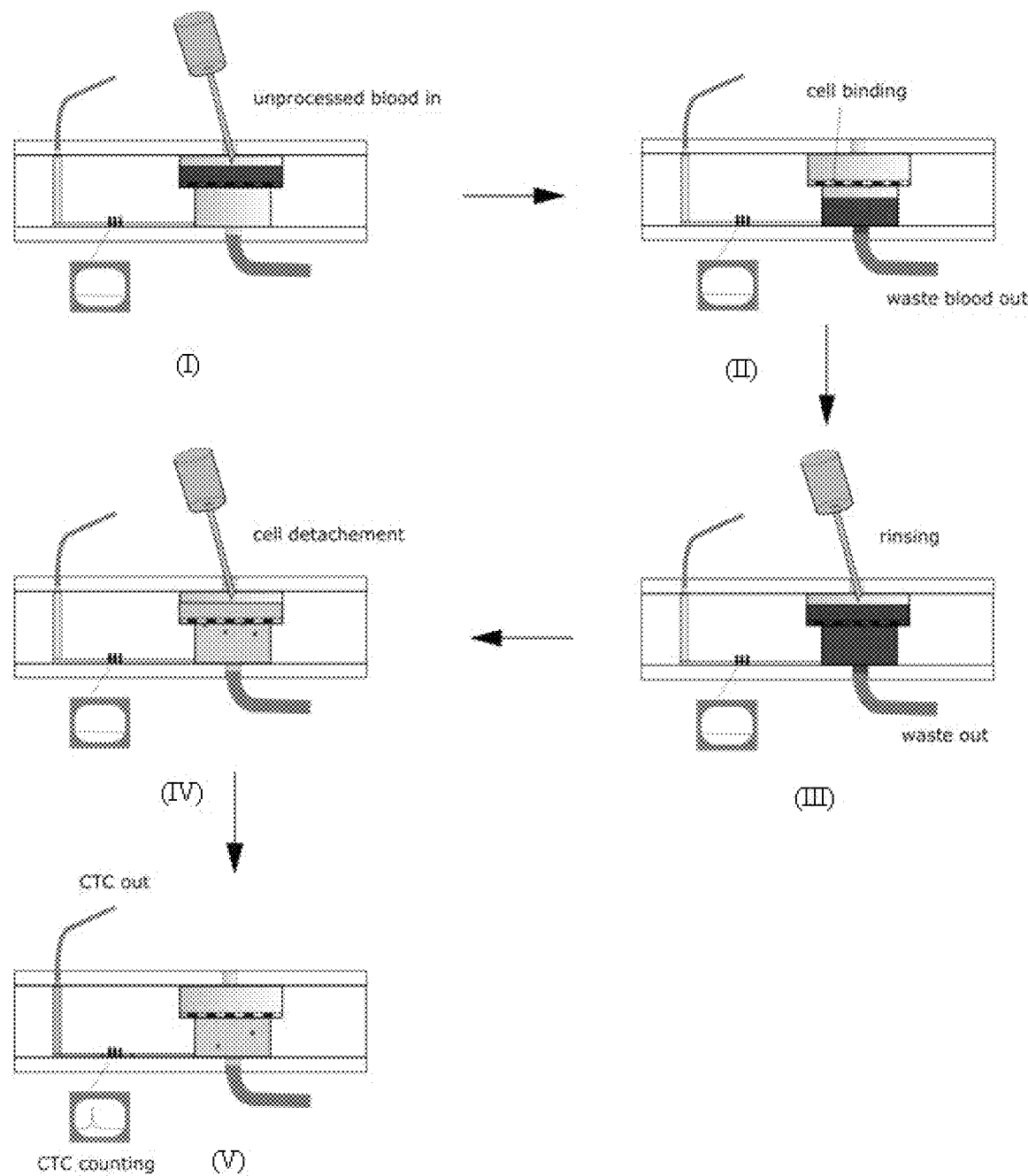
FIG. 5 shows a typical workflow of sorting circulating tumor cells by using the apparatus shown in FIG. 2.

As shown in FIG. 5, in the step of (I), inject unprocessed blood in the cavity 10 though the inlet 11 via a pump;

in the step of (II), pump down the unprocessed blood through the functionalized mesh 20 so that the CTCs bind to the functionalized mesh 20, reverse the operation of pump to get the blood pass though the functional;

in the step of (III), rinse the functionalized mesh 20 in ultra-pure water or other mild solvent to remove all unbound debris, cells or molecules through the first outlet 12;

in the step of (IV), close the first outlet 12 and inject cell detachment buffer (e.

g. a buffer containing trypsin) to get the CTCs captured by the mesh 20 detached from the mesh 20; and in the step of (V), collect the CTCs through the microfluidic channel 13 and count the numbers of said CTCs passing though by the electrodes for impedance measurement arranged in the microfluidic channel 13. After counting, said CTCs is flow out though the second outlet 14.

Said method is aimed at the requirement of early qualitative and quantitative detection of tumor. The mesh with antibodies is designed by the specific antibody technique. The antibodies are used to screen to ensure a high sensitivity, specificity and cell activity. At the same time, combining the mesh with antibodies and microfluidic technology improves the specific surface area and thus increase the flux. A). as there are significant differences in size of the circulating tumor cells and most of the blood cells, and the circulating tumor cells are easily deformed. An array of at least one said mesh can separate CTCs and retains live cells for subsequent monitoring. B). the anti-EnCAM antibodies are attached to the mesh to make sure a high specificity for cells captured. C). the method using the mesh increases the flux, reduces the amount of sample, and the single sample operation time will be reduced to ⅓ of the traditional magnetic beads method. Further, the channel of injection can be multiplied to further reduce the average operating time.

EXAMPLE 1

Herein, a preparation example of the functionalized mesh 20 using for sorting CTCs is given. The preparation method comprises:

(I) choice of the mesh;
gold mesh, the openings (such as, 64 μm or 40 μm) of the gold mesh are chosen so as to maximise the contact time with circulating cells while preventing the risk of clogging. The size of the gold mesh used in the following test was 2×2 mm squares. Larger size is preferred considering manipulation.

Stainless steel and gold mesh, with 51 μm openings coated with AuPd using magnetron sputtering were also used for that purpose. Such meshes are cheaper and mechanically more stable than their gold counterparts, therefore they are better suited for integration into the proposed apparatus.

(II) pre-functionalization preparation:
A number of cleaning methods were used to prepare the mesh prior to functionalization, including autoclaving, oxygen plasma cleaning, and sonication in various solutions, including piranha solutions. If, for example, the best results for the 64 μm gold mesh 20 consists of 15 minute sonication (US) in detergent, rinsing, 15 minutes US in 70% ethanol solution, rinsing, 5 minutes high-purity water. Shorter times can also be expected with harsher solutions (e.g. Piranha).

(III) Antibody;
Typically, 10 μl of antibody was aliquoted out and frozen, and used subsequently to make reaction mixture (i.e. antibody+PBS with EDTA), which is enough for 2×50 μl (50 μl being the minimum volume to immerse a gold mesh 20 of roughly 2 mm square).

(IV) Traut's reagent;
aliquoted and frozen rapidly after purchase. Concentration of traut's reagent was 4:1 ratio compared to the antibody. Other strategies, including thiolated biotin-avidin linker could replace the traut's reagent to attach the antibody to the mesh to form the functionalized mesh.

(V) Incubation time of traut's reagent with antibody;
(V) Optimum reaction time was found to be 1 hour. The time can be shortened in appropriate conditions. Incubation of above solution with mesh 20;

various incubation times (ranging from 10 minutes to 12 hours) and different conditions (4° C., room temperature and 37° C.) were tested. The best compromise is 1 hour at room temperature (small improvements were observed for longer incubation times, but were not significant).

EXAMPLE 2

Experiments were run to validate the efficiency of the mesh to capture EpCAM expressed by cancer cells. The openings are 51 μm in this case. Cell choice—circulating tumor cells having high expression level of the EpCAM protein (e.g. CaCo2 and MCF7 cells) were used.

Cell growth—grown at 37 degrees in DMEM buffer.

Preparation of cell and incubation of mesh-cells were trypsinised and passaged into 1:2 for CaCo2 and MCF7 cells. Tests were also performed on a rotating hot plate at 37° C. After detachment, the cells are diluted 1:10 in DMEM buffer and 0.5 ml was used to incubate the functionalized mesh. Incubation time was 1 hour.

Washing of non-specifically bound cells: the mesh was rinsed using ultra-pure water, incubated in ultra-pure water solution for 2 minutes and rinsed again prior to microscope inspection.

Figure 6A:
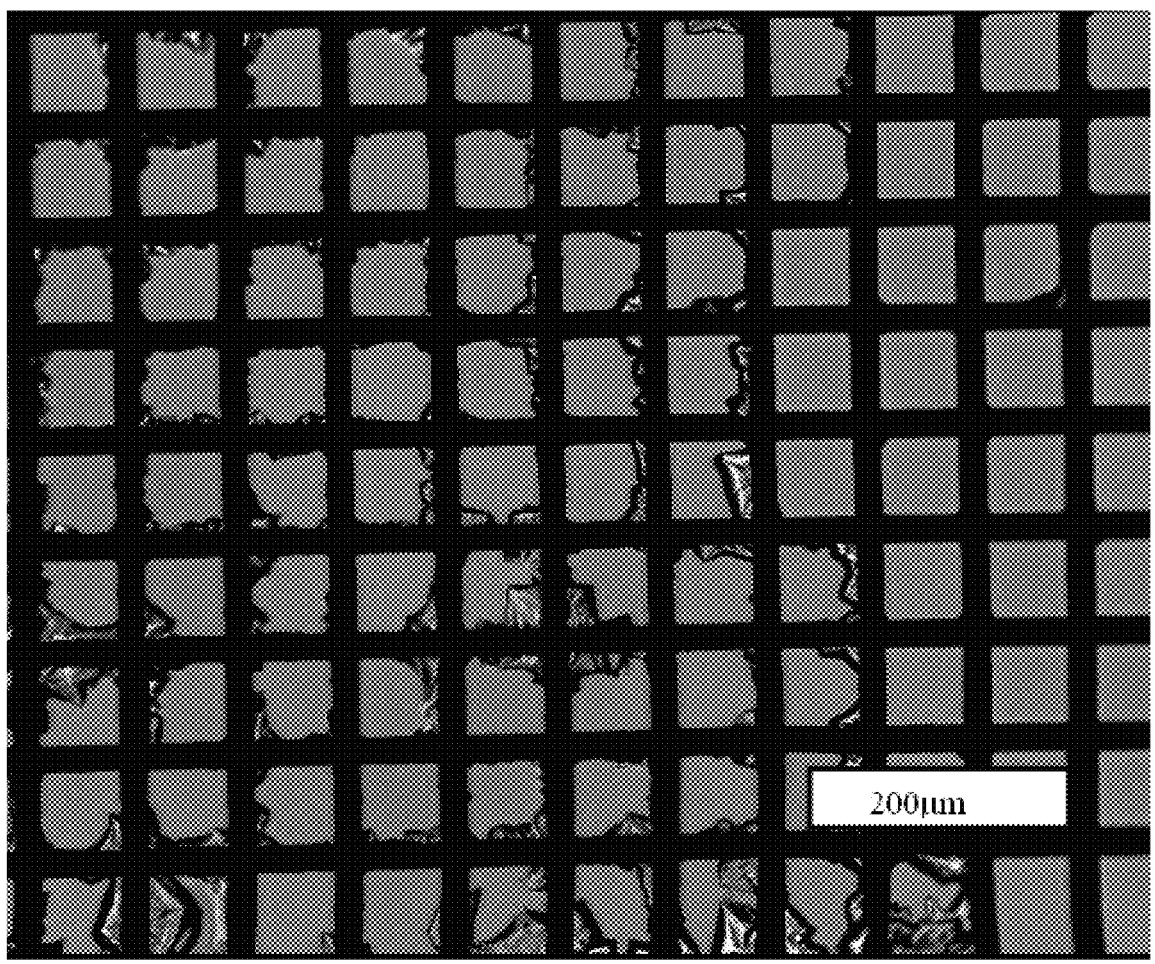
FIGS. 6a and 6b are images showing two kinds of circulating tumor cells expressing target capture molecule captured on functionalized mesh.
Figure 6B:
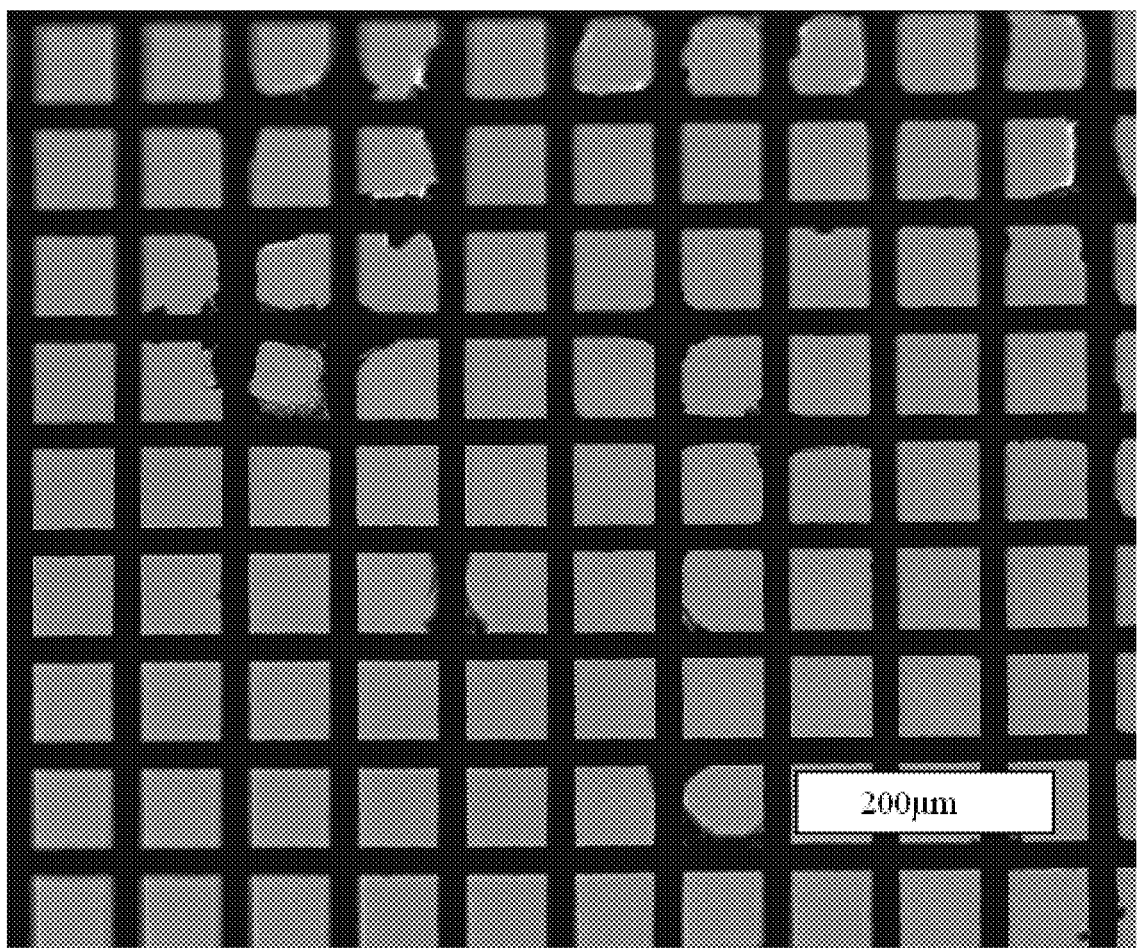

Evaluation of the captured cells using microscopy: Images of the mesh (FIG. 6) are taken by microscopy. FIG. 6a shows CaCo2 cells expressing target capture molecule captured on functionalized mesh after 1 hour incubation, and FIG. 6b shows MCF7 cells expressing target capture molecule captured on functionalized mesh after 1 hour incubation. It can be seen from FIGS. 6a and 6b that a mass of CaCo2 and MCF7 cells were captured by the mesh due to the binding of EpCAM of cells and the anti-EpCAM antibodies on the mesh, while the mesh is not clogged. It should be noted that the method according to the present disclosure can be used to capture target molecules in solution of various concentration.

The embodiments described above are only for illustrating the technical concepts and features of the present disclosure, and intended to make those skilled in the art being able to understand the present disclosure and thereby implement it, and should not be concluded to limit the protective scope of this invention. Any equivalent variations or modifications according to the spirit of the present disclosure should be covered by the protective scope of the present disclosure.

What is claimed is:

1. A method for capturing target cells or molecules in solution, comprising steps of:
   (I) introducing medium containing said target cells or molecules into an apparatus comprising a capturing device for capturing said target cells or molecules;
   (II) introducing said medium flow through said capturing device so that said target cells or molecules bind to the capturing device;
   (III) removing unwanted unbound debris, cells or molecules that may have bound non-specifically on said capturing device;
   (IV) introducing said target cells or molecules detached from said capturing device; and
   (V) collecting said target cells or molecules;
   wherein said capturing device comprises at least one functionalized mesh, said functionalized mesh comprises a mesh substrate and a functional layer formed on said mesh substrate, wherein said functional layer comprises capturing substances that are specifically bindable with said target cells or molecules.

2. The method according to claim 1, wherein in the step of (I), said medium is flown into said apparatus by injection or pumping.

3. The method according to claim 1, wherein in the step of (II), said medium is made to flow through said capturing device a couple of times before flowing out of the apparatus.

4. The method according to claim 3, said medium is firstly made to flow positively through said capturing device and then made to flow reversely through said capturing device.

5. The method according to claim 1, wherein in the step of (III), rinsing said capturing device in ultra-pure water or other mild solvent to remove said unbound debris, cells or molecules.

6. The method according to claim 1, wherein in the step of (IV), injecting cell detachment buffer to get the cells or molecules detached from said capturing device.

7. The method according to claim 6 wherein in the step of (IV), said cell detachment buffer contains trypsin.

8. The method according to claim 1, wherein in the step of (V), said target cells or molecules are counted.

9. The method according to claim 8, wherein in the step of (V), counting of said target cells or molecules is achieved by electrodes using impedance measurement or optical methods.

10. The method according to claim 9, wherein said electrodes for impedance measurement are arranged in a microfluidic channel provided inside of said apparatus, and said target cells or molecules are collected through the microfluidic channel.

11. The method according to claim 1, wherein said molecules are proteins, oligonucleotides, enzymes or any combination thereof in solution or expressed at the surface of cells.

12. The method according to claim 11, wherein said molecules are epithelial cell adhesion molecules at the surface of circulating cancer cells, and said capturing substances are anti-epithelial cell adhesion molecule antibodies, which can specifically bind with said epithelial cell adhesion molecule.

13. The method according to claim 1, wherein said anti-epithelial cell adhesion molecule antibodies are attached to said mesh substrate by traut's reagent or thiolated molecules with biotin-avidin.

14. The method according to claim 1, wherein said capturing substances are selected from the group consisting of antibodies, oligonuecleotides and molecularly imprinted polymers.

15. The method according to claim 14, wherein said capturing substances are attached to said mesh substrate by physical adsorption and/or chemical bonding, said chemical bonding is achieved by using thiolated molecules with or without a linker, using traut's reagent, silanisation or click chemistry.

16. The method according to claim 1, wherein said mesh substrate is 2-10 mm×2-10 mm in size and has openings of 20 µm-100 µm.

17. The method according to claim 1, wherein said mesh substrate comprises:
a stainless steel body; and
a surface coating provided on the surface of said stainless steel body;
wherein said surface coating is made of noble metal or alloy thereof, and said capturing substances are attached to said surface coating.

18. The method according to claim 1, wherein said capturing device containing multiple functionalized meshes stacked together.

19. The method according claim 1, wherein said apparatus further comprises a body which has an inlet, a first outlet and a cavity located between said inlet and said first outlet, said capturing device is fixed inside said cavity, said inlet and said first outlet communicate with the cavity, and
in the step of (I), getting said medium into said cavity of apparatus through said inlet; and
in the step of (III), removing unbound debris, cells or molecules through said first outlet.

20. The method according to claim 19, wherein in the step of (V), collecting said target cells or molecules through a microfluidic channel provided inside of said body communicated with said cavity.

* * * * *